(12) United States Patent
Sheehan

(10) Patent No.: US 10,864,122 B2
(45) Date of Patent: Dec. 15, 2020

(54) ABSORBENT ARTICLE PACKAGE WITH ENHANCED OPENING AND RECLOSEABILITY

(71) Applicant: The Procter & Gamble Company, Cincinnati, OH (US)

(72) Inventor: Astrid Annette Sheehan, Symmes Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/525,636

(22) Filed: Jul. 30, 2019

(65) Prior Publication Data

US 2020/0046579 A1  Feb. 13, 2020

(30) Foreign Application Priority Data

Aug. 13, 2018 (EP) ...................... 18188696

(51) Int. Cl.
  *B65D 85/07* (2017.01)
  *B65D 75/08* (2006.01)
  *A61F 13/551* (2006.01)

(52) U.S. Cl.
  CPC .......... *A61F 13/5511* (2013.01); *B65D 75/08* (2013.01); *B65D 85/07* (2018.01)

(58) Field of Classification Search
  CPC ... A61F 13/551; A61F 13/5511; B65D 33/00; B65D 73/00; B65D 75/08; B65D 85/07
  USPC .......................................................... 206/494
  See application file for complete search history.

(56) References Cited

U.S. PATENT DOCUMENTS

| 3,395,852 | A |  | 8/1968 | Koncak | |
|---|---|---|---|---|---|
| 5,036,978 | A |  | 8/1991 | Frank et al. | |
| 5,307,988 | A | * | 5/1994 | Focke | B65D 75/08 |
|  |  |  |  |  | 206/494 |
| 7,198,154 | B2 | * | 4/2007 | Tippey | B65D 21/08 |
|  |  |  |  |  | 206/440 |
| 7,866,473 | B2 | * | 1/2011 | Clark, Jr. | B65D 75/5833 |
|  |  |  |  |  | 206/494 |
| 8,162,142 | B2 | * | 4/2012 | Kobayashi | B65D 75/5827 |
|  |  |  |  |  | 206/494 |
| 2002/0112982 | A1 | * | 8/2002 | Stagray | B65D 75/5838 |
|  |  |  |  |  | 206/494 |
| 2007/0175789 | A1 | * | 8/2007 | Ronnberg | A61F 15/001 |
|  |  |  |  |  | 206/494 |

FOREIGN PATENT DOCUMENTS

EP        2145831         1/2010

OTHER PUBLICATIONS

European Patent Search dated Jan. 29, 2018.

* cited by examiner

*Primary Examiner* — Bryon P Gehman
(74) *Attorney, Agent, or Firm* — Christian M. Best

(57) ABSTRACT

A package containing a stack of folded disposable absorbent articles, the package being formed of a flexible polymeric film defining a cuboid package having top and bottom surfaces and rear, front, first and second side walls. One or more folding tabs are provided proximal the top surface and extending along a width of one or both of the first and second side walls. Each folding tab has a height of between about 10 mm and about 50 mm in a direction perpendicular to the length of the folding tab and comprises a higher bending stiffness than the flexible polymeric film.

17 Claims, 20 Drawing Sheets

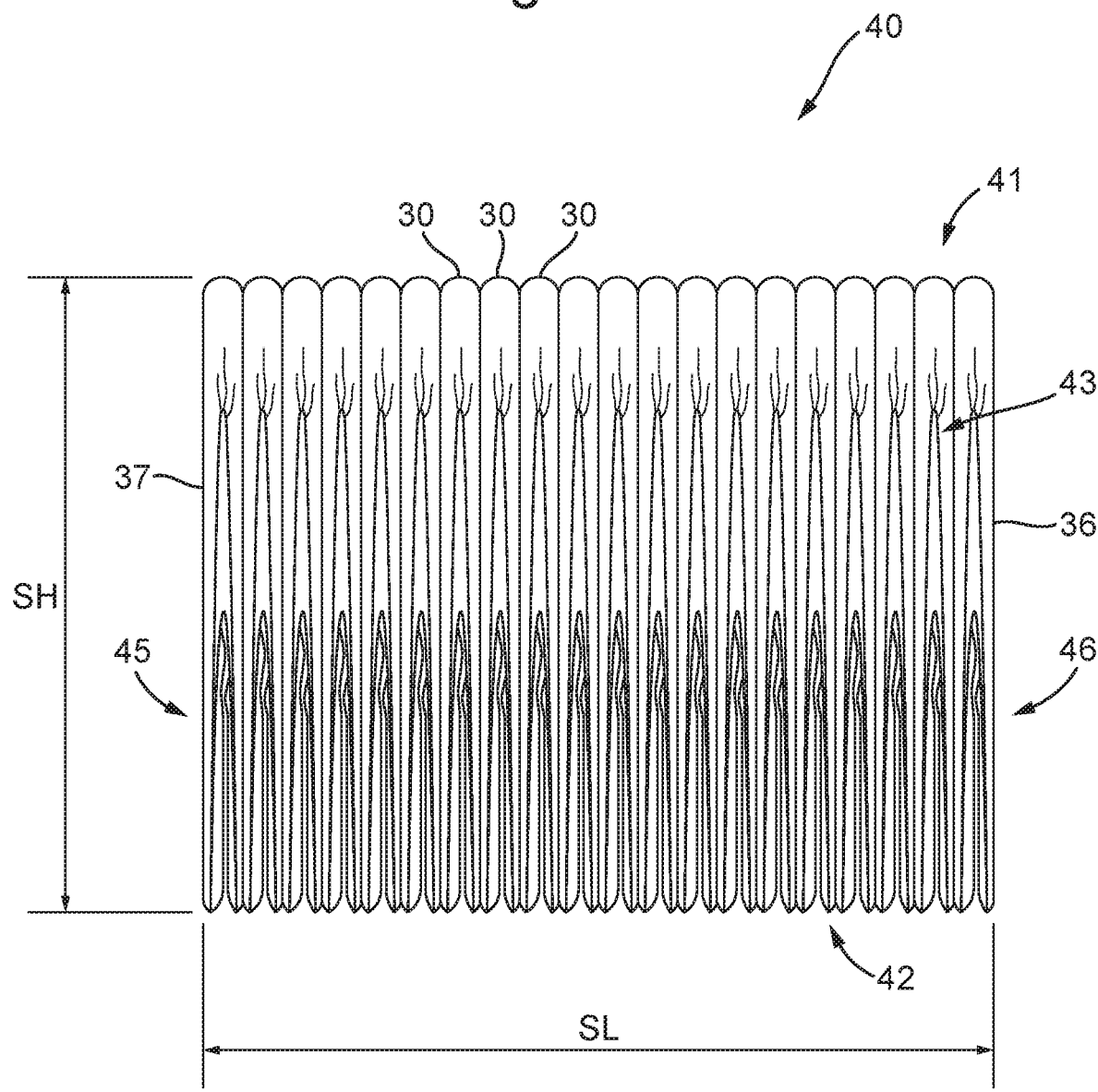

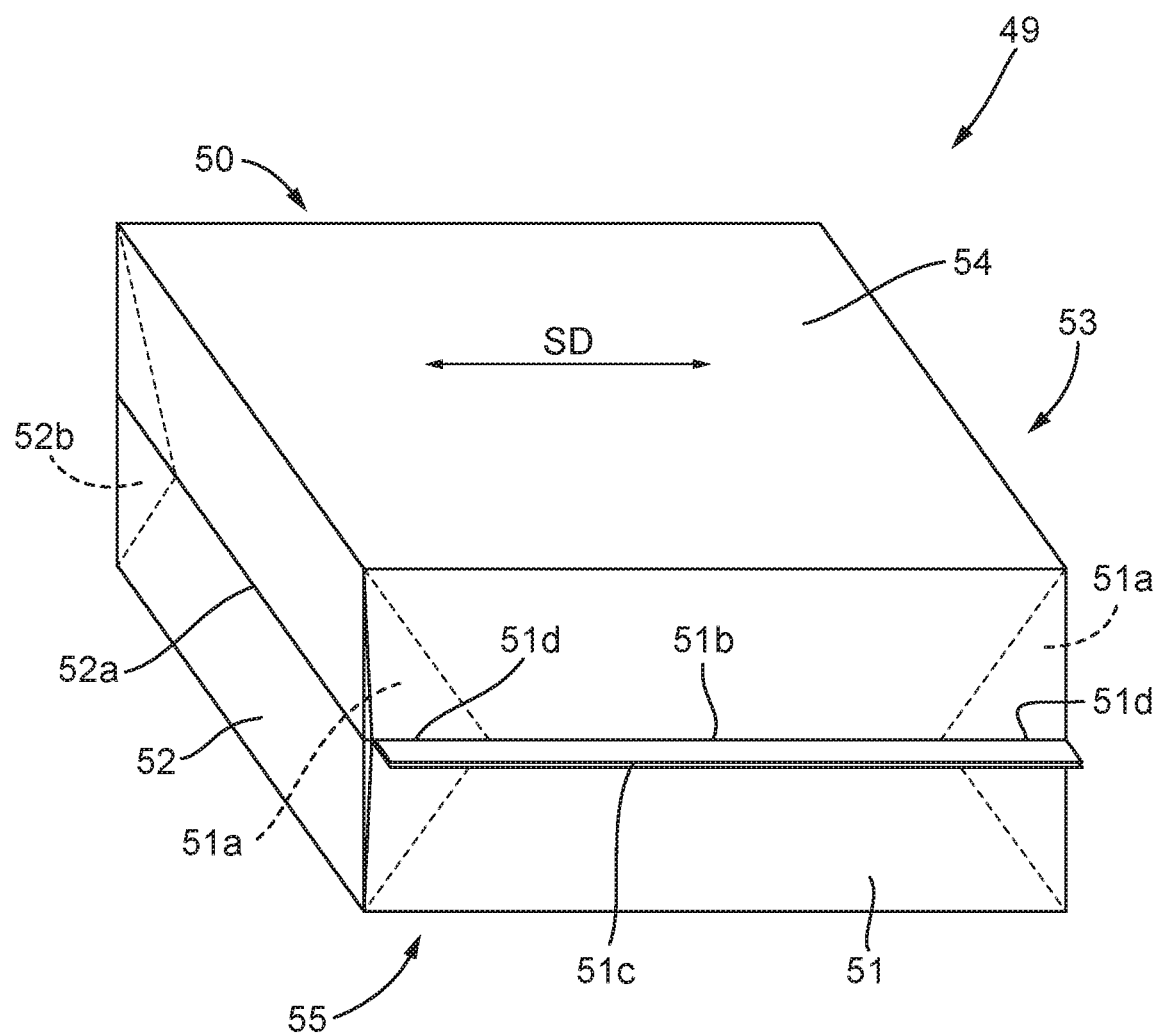

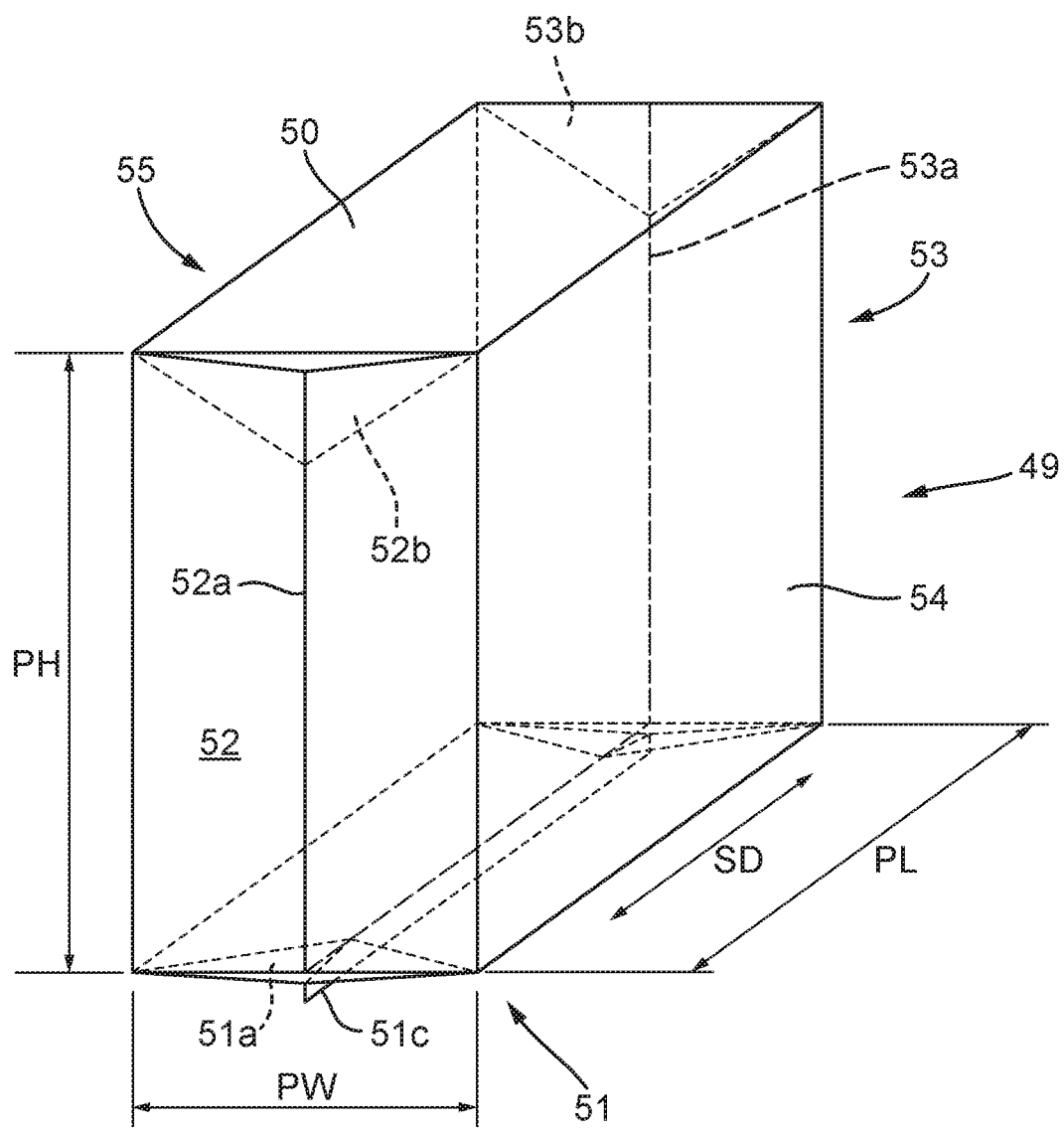

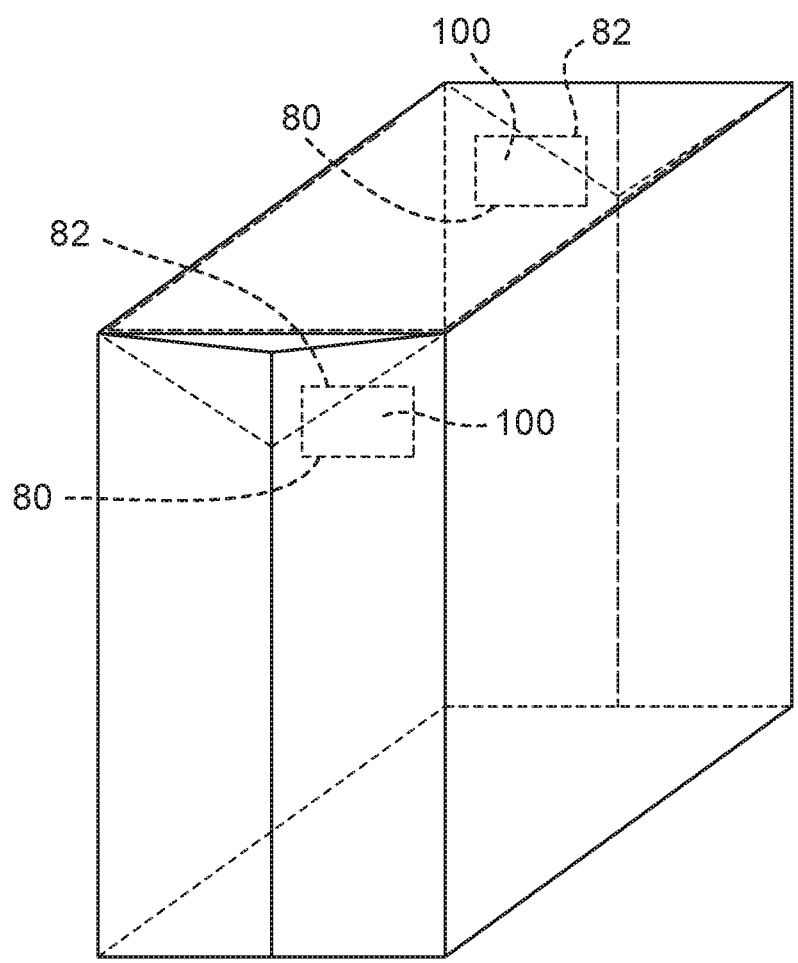

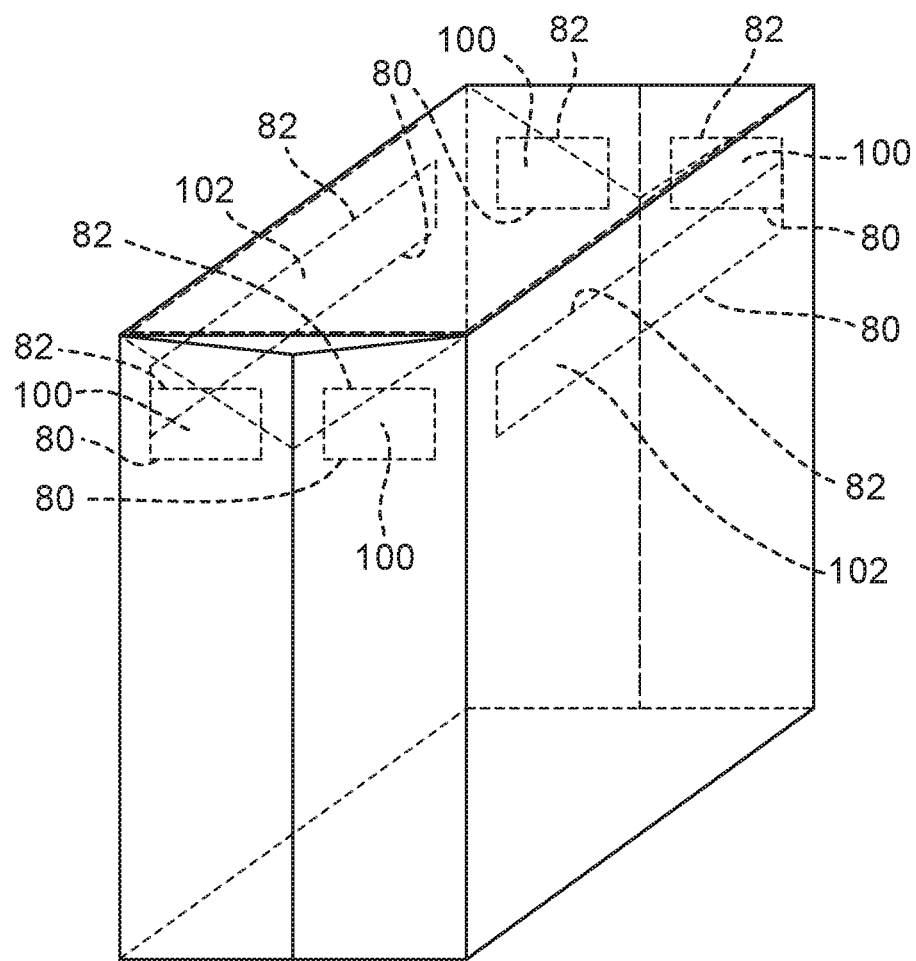

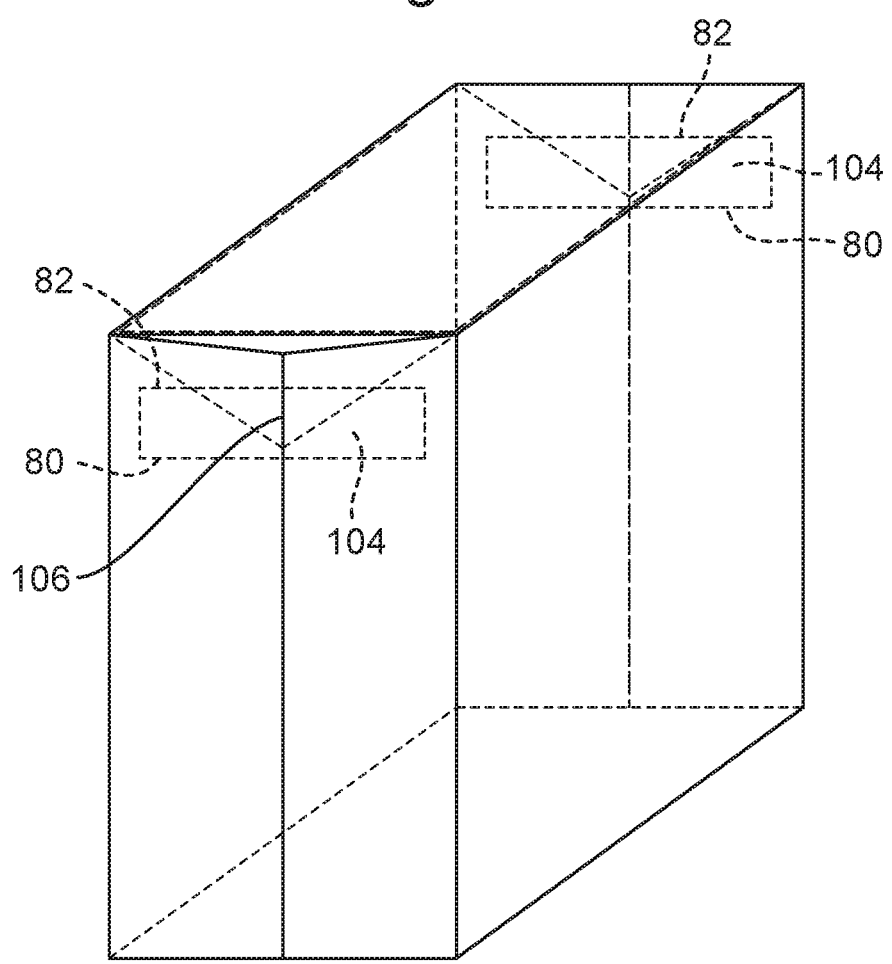

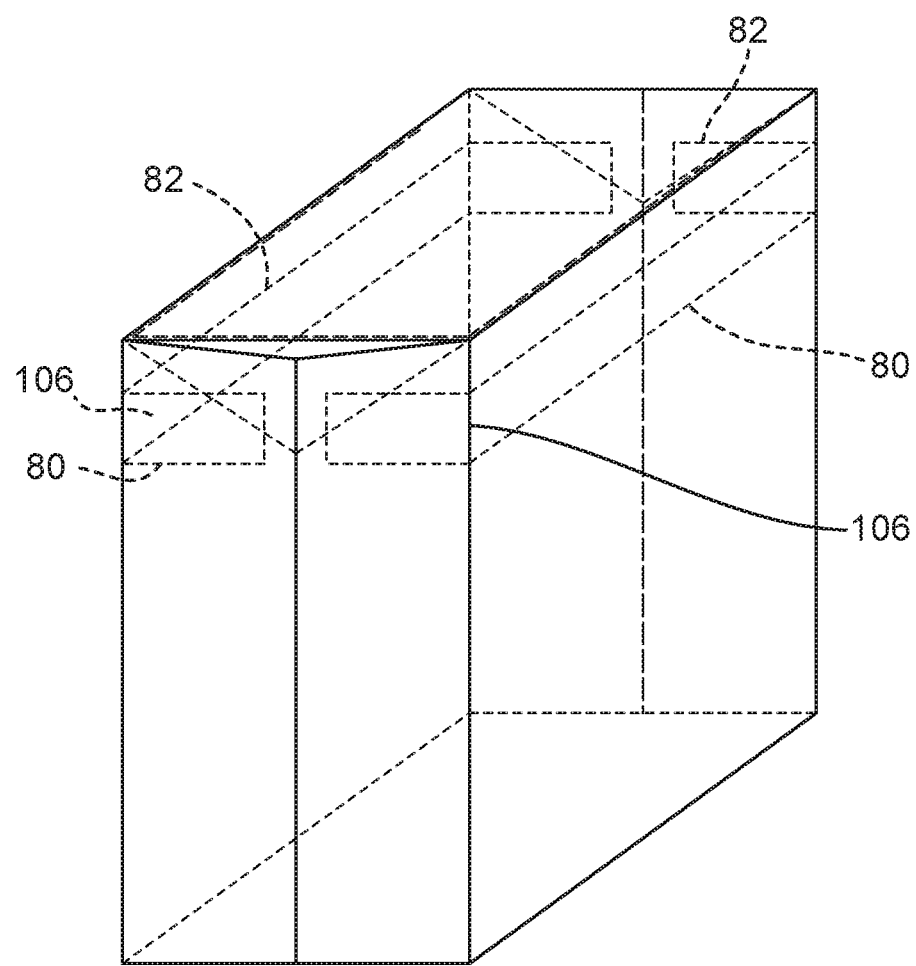

ABSORBENT ARTICLE PACKAGE WITH ENHANCED OPENING AND RECLOSEABILITY

CROSS REFERENCE TO RELATED APPLICATION

This application claims priority under 35 U.S.C. § 119 to European Patent Application Serial No. 18188696.1, filed on Aug. 13, 2018, the entire disclosure of which is hereby incorporated by reference.

BACKGROUND

Non-fragile, compressible consumer products such as disposable absorbent articles (e.g., diapers and training pants, disposable adult incontinence pants and feminine hygiene pads) are often packaged and sold at retail (i.e., placed on display and for sale in a retail store) in soft packages formed of polymer film. Such packages may be formed from one or more sheets of polymer film, seamed via application of heating energy, which causes portions of the film to melt and fuse along the seams.

Typically, the products are sold in large volumes such that they may occupy considerable space in a person's home. After opening a package of disposable absorbent articles and removing one or more items needed for immediate use, a consumer may wish to leave the remaining unused supply of product in the package for storage until the next time additional items are needed. Thus, it is often desirable that the package retain, to some extent, its shape and structural integrity while occupying the least amount of space possible. Furthermore, given the intended use regarding proximity to a body of such disposable absorbent articles, it is desirable for such packaging to be closable in such a way that unused products stored inside the packaging are protected from airborne contaminants.

An additional concern, particularly when considering diapers and training pants, is the ease of being able to access unused products stored inside the packaging. Often, when film packaging is no longer full, the excess film may be scrunched together as a way of "closing" the packaging and preventing contaminants from entering. Thus, it may be difficult for a parent seeking to remove a diaper from the pack while holding onto a child to locate the opening and remove a product.

As set out above, film packaging has been less than optimal for reuse to date. Thus far, various attempts have been made to enhance opening and closing features, e.g., the provision of perforations for easy opening/closing, however, little has been done to facilitate easy compaction and/or closing of such packaging after initial use.

Consequently, there is room for improvement in film package opening features.

BRIEF DESCRIPTION OF THE FIGURES

FIG. 4A is an edge side view of a stack of a plurality of folded diapers such as the folded diaper shown in FIGS. 3A and 3B.

FIG. 5B is a perspective view of a film package that may be used to contain a stack of disposable absorbent articles such as the stack shown in FIG. 4.

FIG. 5C is an alternative perspective view of the film package shown in FIG. 5B.

FIGS. 7A to 7F show schematically different examples of the present invention, including variations in placement of the one or more folding tabs.

DESCRIPTION

Definitions

Figure 1:
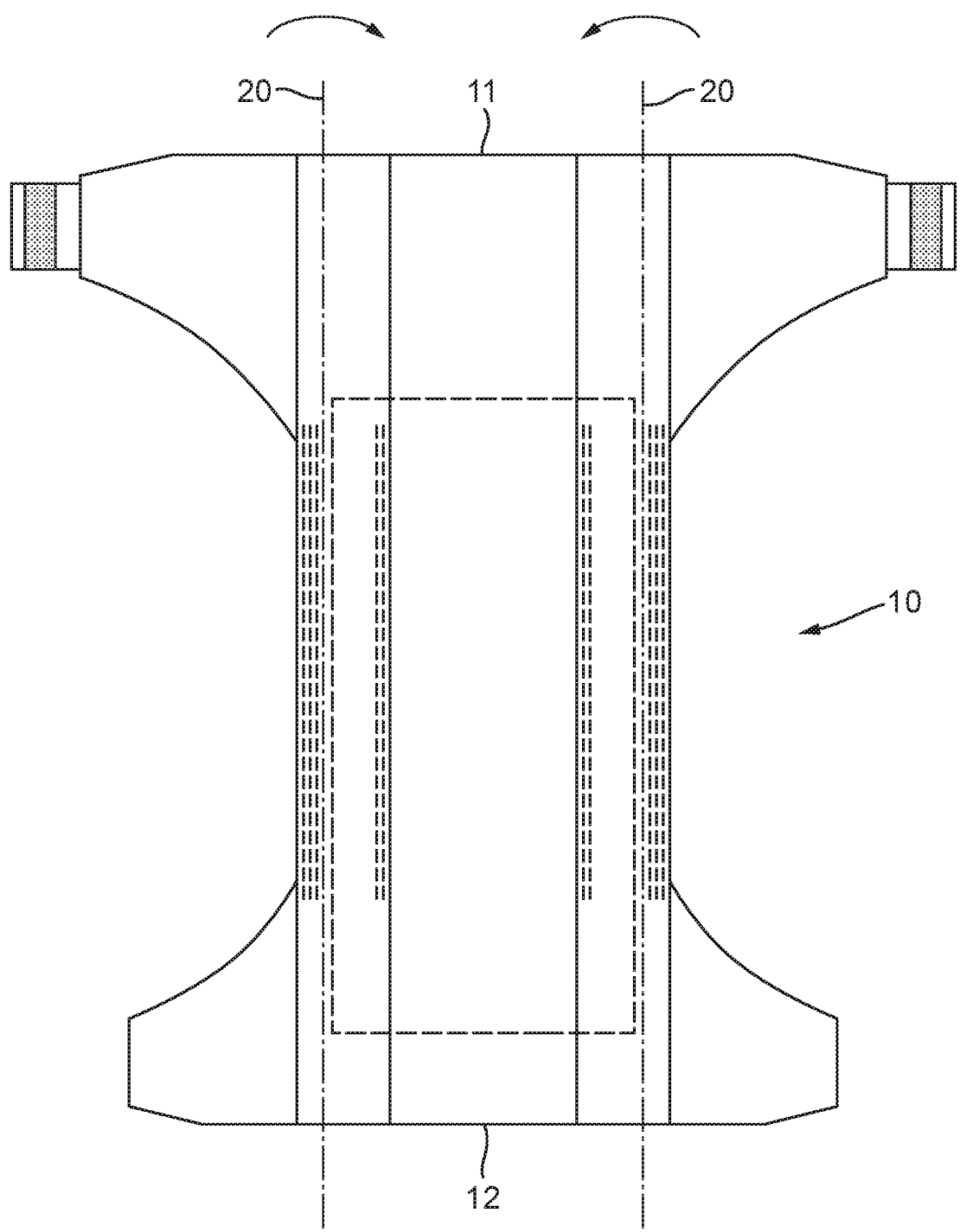
FIG. 1 is a plan view of an example of a disposable absorbent article in the form of a disposable diaper, with the wearer-facing surface facing the viewer.

"Film" means a sheet structure having a length, width and thickness (caliper), wherein each of the length and width greatly exceed the thickness, i.e., by a factor of 1,000 or more, the structure having one layer (monolayer) or more respectively adjacent layers (multilayer), each layer being a substantially continuous structure formed of one or more thermoplastic polymer resins (including blends thereof).

"High Density Polyethylene" (HDPE) means a type of polyethylene defined by a density equal to or greater than 0.941 g/cm$^3$.

"Low Density Polyethylene" (LDPE) means a type of polyethylene defined by a density equal to or less than 0.925 g/cm$^3$.

"Medium Density Polyethylene" (MDPE) means a type of polyethylene defined by a density range of 0.926-0.940 g/cm$^3$.

With respect to a disposable diaper, disposable absorbent pant, or feminine hygiene pad, "lateral" and forms thereof refer to a direction parallel with the waist edges and/or perpendicular to the direction of wearer's standing height when the article is worn.

"Linear Low Density Polyethylene" (LLDPE) means a type of Low Density Polyethylene characterized by substantially linear polyethylene, with significant numbers of short branches, commonly made by copolymerization of ethylene with longer-chain olefins. Linear low-density polyethylene differs structurally from conventional low-density polyethylene (LDPE) because of the absence of long chain branching. The linearity of LLDPE results from the different manufacturing processes of LLDPE and LDPE. In general, LLDPE is produced at lower temperatures and pressures by copolymerization of ethylene and such higher alpha-olefins as butene, hexene, or octene. The copolymerization process produces a LLDPE polymer that has a narrower molecular weight distribution than conventional LDPE and in combination with the linear structure, significantly different rheological properties.

With respect to a disposable diaper, disposable absorbent pant, or feminine hygiene pad, "longitudinal" and forms thereof refer to a direction perpendicular with the waist edges and/or parallel to the direction of the wearer's standing height when the article is worn.

With respect to quantifying the weight fraction or weight percentage of a component of a polymer resin composition forming a film or layer thereof, "predominately" (or a form thereof) means that the component constitutes the largest weight fraction or weight percentage among all components of the composition.

A package according to the present disclosure is provided with one or more folding tabs designed to facilitate easy opening and closing of a film package after initial use. Film packaging is typically flimsy and is usually scrunched together after initial opening to minimise space occupied by the package and to prevent foreign articles from entering the pack and contaminating articles left therein. The folding tabs provide a structure that naturally causes the opening of the film package to come together in a way that can be neatly folded over itself to reduce space occupied by the package (particularly once products have been removed) and thereby preventing dust or other articles from entering the package while not in use.

It will be appreciated that the folding tabs may take a multitude of forms while providing the benefits described above, for example a single folding tab may be used or multiple folding tabs may be used. In general, however, one or more folding tab(s) is provided along at least one wall of the film package proximal to and in a direction substantially parallel to an opening of the film package (described in more detail later) with gaps or weakened portions provided in the folding tab(s) at the corners or seams (i.e., any part of the packaging that is not a planar surface). The folding tab(s) are formed of material that is stiffer than the film package principle material and have a minimum height (measured in they direction) about which the package may be folded. The inventors have found that the folding tab provides some weight to the film package, causing the open ends of the package to gravitate towards one another. Once brought together, the film package may be folded about the folding tab, effectively sealing the film package. The height of the folding tab determines the number of folds needed to fully compact the film package to its minimum possible size.

Packaging Film

Referring to FIGS. 1 to 5C, a retail package 49 (shown in FIG. 5B) of non-fragile, compressible disposable absorbent articles 10 (such as, for example, disposable diapers, training pants, adult incontinence pants, and sanitary pads) may be formed of a polymer film. The film may be a single layer (monolayer), or may have two, three or more layers (multilayer). A multilayer film may have, for example, an outer skin layer formed of a first polymer and an inner skin layer formed of a second polymer. (As used herein, the terms "outer" and "inner" refer to the positioning of the layer relative the inside and the outside of the finished package; thus, the "inner layer" faces the contained product, and the "outer layer" faces outward and has an outer surface that is exposed to view and touch by, e.g., shoppers in a retail store.)

Figure 2:
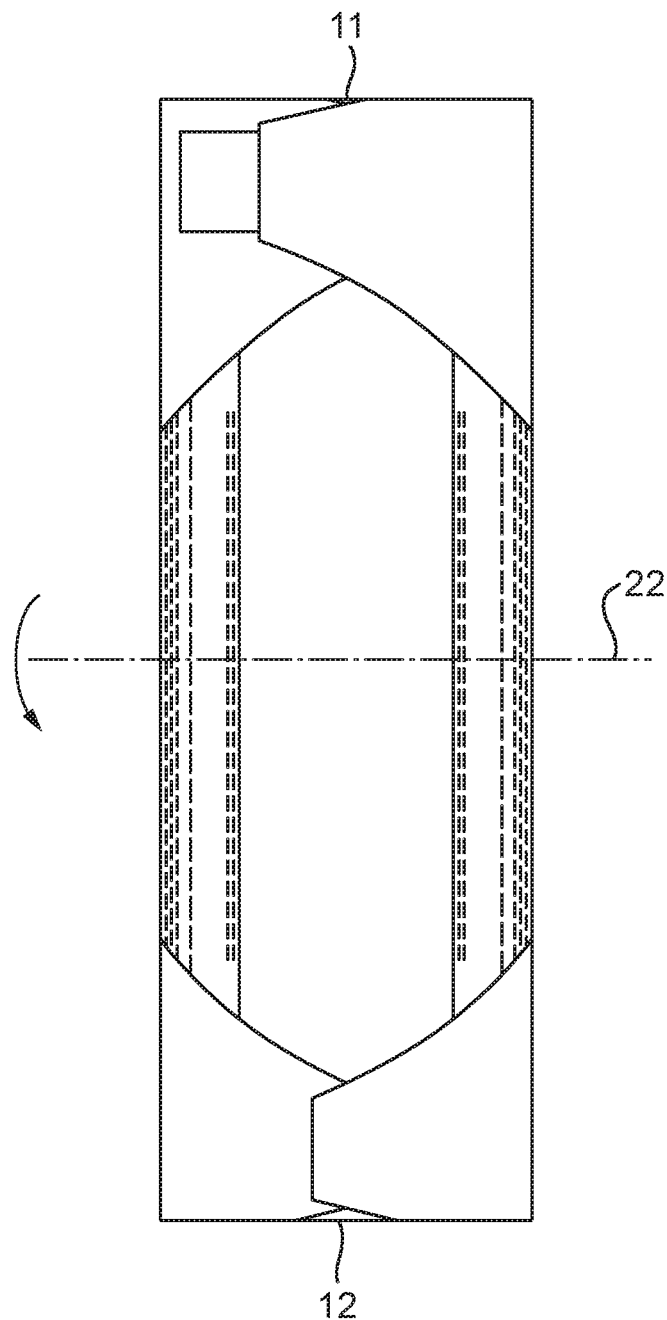
FIG. 2 is a plan view of the diaper of FIG. 1, shown with side portions folded over and laterally inward about longitudinal side edge fold lines.
Figure 3A:
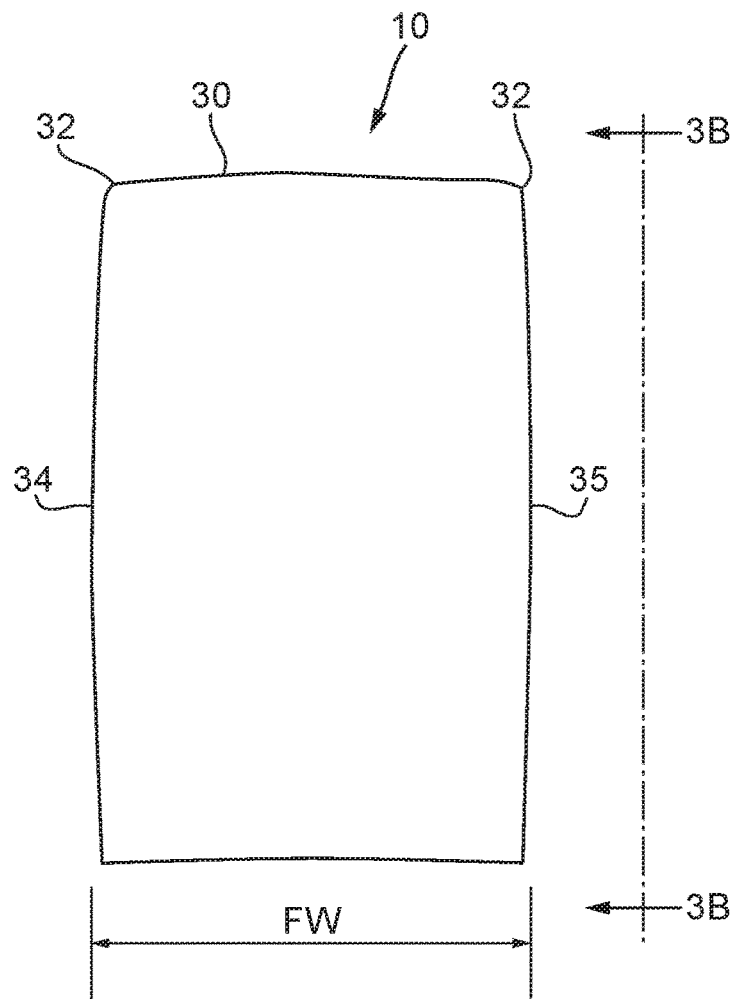
FIG. 3A is a plan view of the diaper of FIG. 2, shown folded about a lateral fold line, wearer-facing surfaces in and outward-facing surfaces out.
Figure 3B:
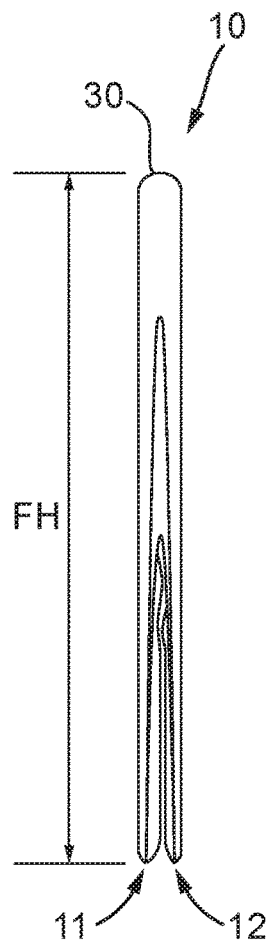
FIG. 3B is an edge side view of the folded diaper shown in FIG. 3A.
Figure 4B:
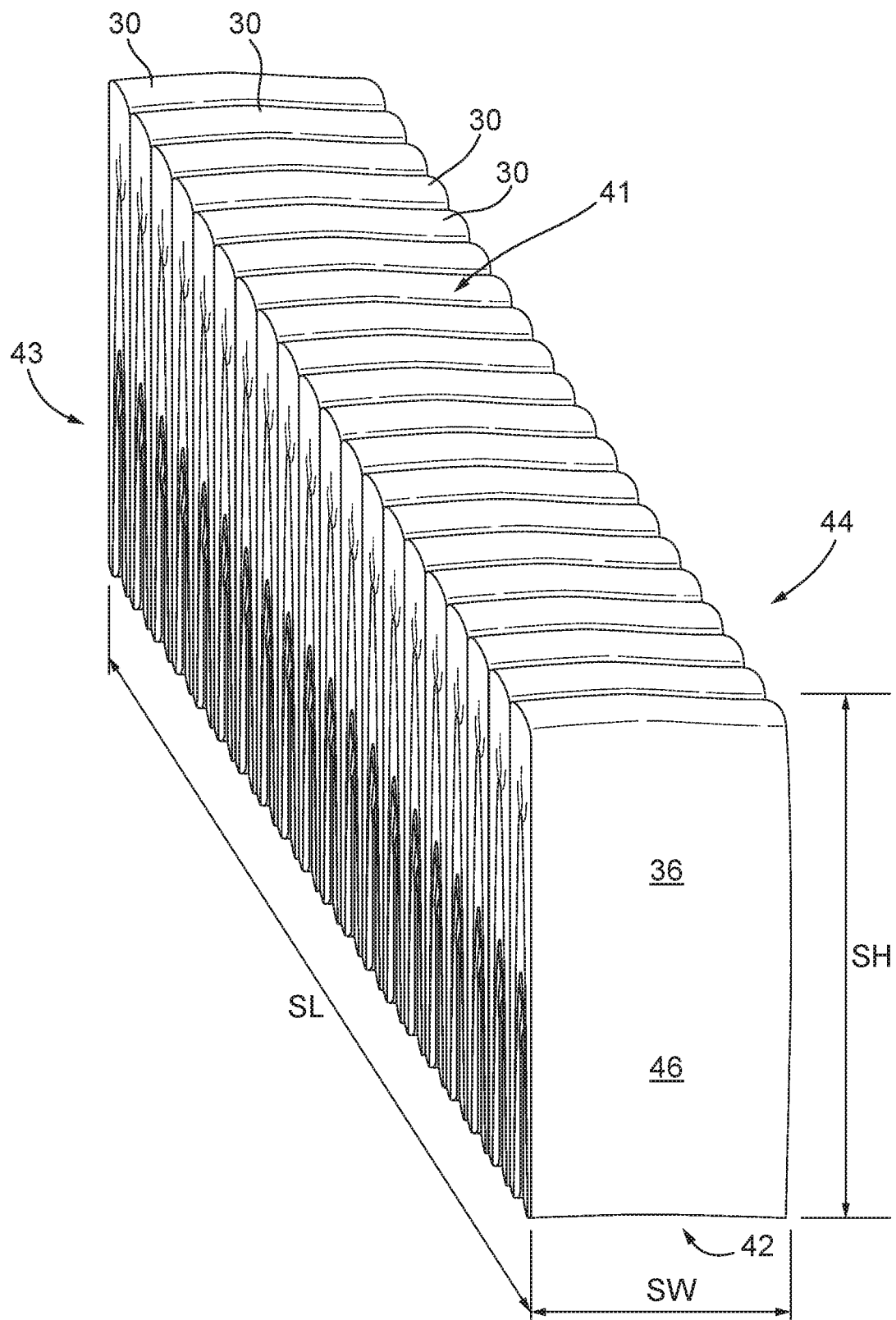
FIG. 4B is a perspective view of the stack of FIG. 4A.

FIGS. 1-3 depict an example of a disposable diaper 10 with front and rear waist edges 11, 12, in successively open/unfolded and folded states. FIGS. 4A and 4B depict a stack of a plurality of disposable diapers 10 such as that depicted in FIGS. 1-3. For packaging in bulk, each of a plurality of disposable diapers such as that shown in FIG. 1 may, in a possible first step, have its longitudinal side portions folded over and laterally inward about longitudinal side edge fold lines 20, as may be appreciated from a comparison of FIGS. 1 and 2. Next, the diaper may, in a second step, be folded longitudinally, about lateral fold line 22 that passes through the crotch region of the diaper, as may be appreciated from a comparison of FIGS. 2 and 3. For a bi-fold configuration such as depicted in FIGS. 3A, 3B and 4, the article may be folded longitudinally once, and may in some examples be folded approximately in half about the lateral fold line. For a tri-fold configuration (not shown), the article may be folded longitudinally twice, about two longitudinally-spaced lateral fold lines. In some examples a tri-fold configuration may have the article folded approximately in thirds, about the two longitudinally-spaced lateral fold lines.

Regardless of whether the article is in a bi-fold or tri-fold configuration, the folded article such as folded diaper 10 will have a single fold nose 30 defining at least one end edge of the folded article, fold nose corners 32, and left and right side edges 34, 35. (It will be appreciated that in a tri-fold example, a single fold nose may define each of both end edges of the folded article.) In some examples such as depicted in FIGS. 3A and 3B, fold nose 30 may be proximate the crotch region of the article (the middle region of the article adapted to be located between the wearer's legs during wear). The folded article will have a folded width FW measured as the distance between side edges, and a folded height FH measured as the distance between end edges. A plurality of folded articles such as depicted in FIGS. 3A and 3B may then be placed in similar orientation and neatly stacked together face-to-face to form a stack 40 such as depicted in FIGS. 4A and 4B. In another example (not shown), a first set of the plurality of folded articles may have their fold noses oriented along one side of the stack, and a second set of the plurality of folded articles may be rotated 180 degrees to have their fold noses oriented along the opposite side of the stack. In some examples, the articles in the first set and the articles in the second set may appear in alternating sequence in the stack. For purposes of economy of space in packaging, packing, shipping and shelving, stack 40 may be compressed to a desired degree of compression, along the stack direction SD.

Referring to FIGS. 4A and 4B, stack 40 will have an approximate rectangular cuboid form with a stack height SH approximately corresponding to the folded height FH of the individual folded articles, a stack width SW approximately corresponding to the folded width FW of the individual folded articles, and a stack length SL measured from a first outward-facing side 36 of a first article in the stack to an opposing second outward-facing side 37 of a last article in the stack, along stacking direction SD. Stack 40 may have a first side 41 and an opposing second side 42, one or both of which are defined by approximately aligned fold noses of folded articles in the stack. Stack 40 may have opposing third and fourth sides 43, 44, both of which are defined by approximately aligned side edges 34, 35 of folded articles in the stack. Stack 40 may have opposing fifth and sixth sides 45, 46, each of which is defined by one of first and second outward facing sides 36, 37 of first and last articles at each end of the stack.

Figure 5A:
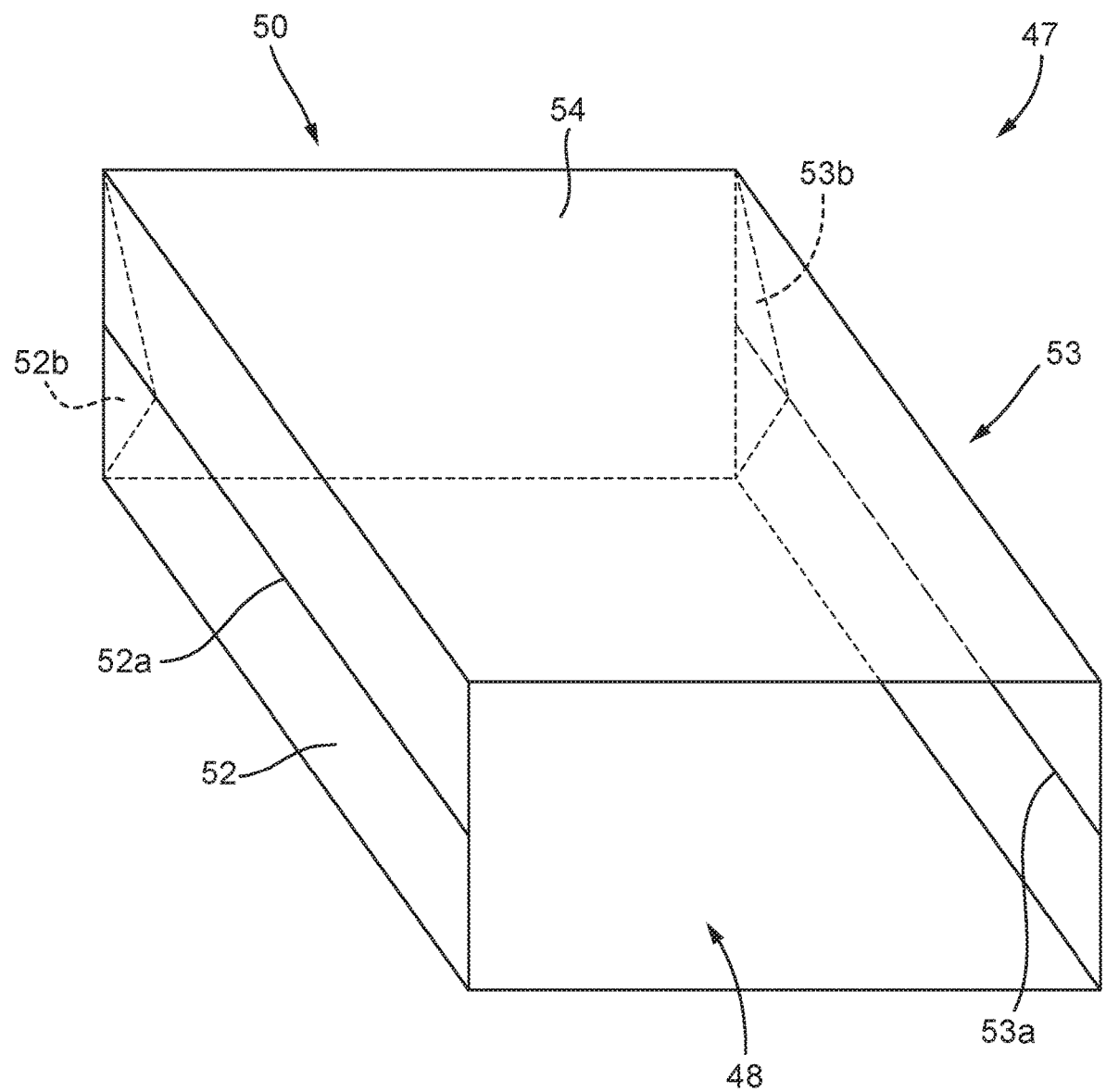
FIG. 5A is a perspective view of a film bag structure from which a film package may be formed.

Referring to FIG. 5A, a bag structure 47 may be formed from a single sheet of film stock that is suitably folded to form bag gussets 52b, 53b and then joined along portions by bonding to form two side seams 52a, 53a on opposite sides, to form bag structure 47 with no seam on a first package surface 50, and open at the other end 48 (e.g., a gusseted bag structure). Thereafter, the bag structure may be filled by inserting product such as stack 40 of diapers through the open end 48. In a first example, stack 40 of diapers may be inserted first side 41 first, such that after insertion the fold noses inside the package are adjacent first package surface 50. In another example, stack 40 of diapers may be inserted first side 41 last (i.e., second side 42 first), such that after insertion the fold noses inside the package are adjacent second package surface 51. As may be appreciated from FIGS. 5B and 5C, the open end 48 opposite first package surface 50 may then be closed by suitably folding to form closing gussets 51a, bringing the film edges together, and bonding them together to form end seam 51b and second package surface 51. The bag structure 47 and stack 40 dimensions may be suitably selected and effected through design, folding, stacking, compression and packaging processes such that the film of the package is taut about the stack at least along the stacking direction SD, to retain the individual diapers 10 in place within the stack 40, maintain stack compression, and maintain a neat, stable, approximate rectangular cuboid shape for the stack 40, and as a result, the package 49. Because the package 49 is formed of flexible polymer film, when suitably sized relative to the stack 40 dimensions, package 49 will assume the approximate rectangular cuboid shape and dimensions of the stack 40, when the package film is taut, or otherwise when any loose film is pressed against the stack. When the package film is taut about the stack along directions generally parallel with the stacking direction, in a manner that helps maintain stack compression along the stacking direction, the package will have a package length PL approximately corresponding to the stack length SL, and a package width approximately corresponding to the stack width SW. If the package structure is sized to provide no head space adjacent one or both of first and second sides 41, 42 of packaged stack 40 (i.e., no slack is present in the package film adjacent first and second sides 41, 42 of the stack after the package 49 is formed), the package will have a package height PH approximately corresponding to the stack height SH. In some examples, however, the film package structure may be sized to provide head space, and correspondingly, slack film, adjacent one or both of the first 41 and second 42 sides of stack 40, such as may be desired to provide a hood structure (described below) with extra height and overlapping capability.

To which reference is made above, the left and right side edges 34, 35 of the folded diapers in the stack 40, and corresponding third and fourth sides 43, 44 of stack 40 will be adjacent fifth and/or sixth package surfaces 54 and 55. It may be desired that the stack size and bag configuration and dimensions be selected such that fifth and sixth package surfaces 54 and 55 are the largest surfaces, or front and rear "faces," of the package. In this arrangement, when the film of the package is taut about the stack, the film of the third, fourth, fifth and sixth package surfaces 52, 53, 54 and 55 is in tension along directions approximately parallel to the approximate plane of the first surface 50, serving to at least partially maintain any compression of the stack 40 along the stacking direction SD.

It will be appreciated that the stack of folded diapers may be alternatively oriented, for example, where the noses of the folded diapers are located in line adjacent one of the gusseted sides of the package. The final package 49 has a generally cuboid shape having a front surface 54, rear surface 55, top surface 50, bottom surface 48, first side surface 52, and second side surface 53. The package has a package height PH and package width PW (as seen, for example, on shelf). Two seams 52a and 53a are provided on the first and second side surfaces about which the package may be folded.

In some examples, the film stock may be supplied preprinted with desired commercial artwork, graphics, trademark(s) and/or verbal or graphic product information, prior to formation of the bag structure.

The bonds forming any or all of the seams such as seams 52a, 53a and 51b may be created by welding. (Herein, "weld" refers to a union between separate portions of film stock, effected by application of direct or indirect (e.g., ultrasonic) heating energy and pressure that causes separate portions of the film to at least partially melt and fuse together to some extent, forming a bonded area, joint or seam which cannot be separated without substantial destruction to the remainder of one or both joined portions.) If bag-forming and/or packaging machinery forms welds in the film that join the film stock to itself by applying heating energy that causes the film to fuse to itself, it may be desirable that the film stock be multilayer film, and that the layer(s) to be brought into contact and fused be formed of polymer(s) that have lower melting temperature(s) than those of the polymer(s) used to form the other layer(s). This enables heating energy to be applied to a degree sufficient to heat the layer(s) in contact and cause them to fuse, but not sufficient to cause undesired melting and deformation of the other layer(s), which could cause the package to be misshapen and/or displace and/or distort printing on the film stock.

A multilayer film may be co-formed (such as by coextrusion), or in another example, individual layers may be separately formed and then laminated together following their formation, by use of a suitable laminating adhesive. In this latter example, an advantage provided is that one of the layers may be printed on one side before lamination. Following that, the printed side may be faced inward (facing the other layer(s)) during lamination, such that it is protected by the other layer(s) from abrasion and wear in the finished film product, thereby preserving the integrity of the printed images, graphics, verbal content, etc. A suitable multilayer film may be formed of one or more polyolefins, such as polypropylene and polyethylene. In one example, the stock film may have at least two layers, including a first layer of predominately polyethylene and second layer of predominately polypropylene. In one example, a layer formed of predominately polypropylene having a first relatively higher melting temperature, and a layer of predominately polyethylene having a second relatively lower melting temperature, may be used to form the outer and inner layers, respectively. In another example, an inner layer may be formed predominately of a first type of polyethylene having a relatively lower melting temperature, and an outer layer may be formed predominately of a second type of polyethylene having a relatively higher melting temperature.

In an application such as described herein, a multilayer film may be desired. A multilayer film may have layers of polymer compositions particularly chosen for the characteristics they impart to the film. For example, one or two outer skin layers may be formed of compositions chosen for, e.g., surface gloss; printability; smooth feel; pliability; low noise generation (upon being handled and manipulated, as by a consumer); relatively lower melt temperature and fusibility/weldability; or any combination of these characteristics. One or more intermediate layers may be formed of compositions chosen for, e.g., tensile strength; stiffness; toughness; suitability for inclusion of blended-in recycled material; environmentally-friendly and/or sustainable material sourceability; relatively higher melt temperature; co-extrusion compatibility with adjacent layers (such that strong bonding between layers occurs upon co-extrusion); or any combination of these characteristics. For film stock in which only one side of the film will be placed in contact with itself and welded, a two-layer film may suffice. For film stock in which both sides of the film will be placed in contact with itself and welded, a film having at least three layers, with two outside skin layers that are weldable, may desired. It will be appreciated that a package having the configuration depicted in FIGS. 5B and 5C requires the film to be welded to itself on both sides—on the generally outer film surface at the gussets 51*a*, 52*b* and 53*b*, and on the generally inner film surface along all other portions of the seams 51*b*, 52*a* and 53*a*.

Film Composition

A multilayer film may include first outside skin layer, second outside skin layer, and intermediate layer disposed between the skin layers.

Each of the layers may include a base polymer. Base polymers may include polyolefins, particularly polyethylenes, polypropylenes, polybutadienes, polypropylene-ethylene interpolymer and copolymers having at least one olefinic constituent, and any mixtures thereof. Certain polyolefins can include linear low density polyethylene (LLDPE), low density polyethylene (LDPE), medium density polyethylene (MDPE), high density polyethylene (HDPE), isotactic polypropylene, random polypropylene copolymers, impact modified polypropylene copolymer, and other polyolefins which are described in PCT Application Nos. WO 99/20664, WO 2006/047374, and WO 2008/086539. Other base polymers such as polyesters, nylons, polyhydroxyalkanoates (or PHAs), copolymers thereof, and combinations of any of the foregoing may also be suitable. In addition, polyolefin plastomers and elastomers could be used to form the multilayer polymeric films. Examples of such suitable polyolefin plastomers and elastomers are described in U.S. Pat. No. 6,258,308; U.S. Publication No. 2010/0159167 A1; and PCT Application Nos. WO 2006/047374 and WO 2006/017518. In one embodiment, such polyolefin plastomers and/or elastomers may comprise up to 25% by volume of the multilayer polymeric film. Other useful polymers include poly-α-olefins such as those described in PCT Application No. WO 99/20664 and the references described therein.

In some examples, one or both of the skin layers may be formed of predominately MDPE, LDPE or LLDPE, or LLDPE. A skin layer formed of predominately LLDPE may be particularly desired because it imparts the skin layer with a good combination of weldability, relatively low melt temperature, printability (compatibility with currently commercially available printing inks), smooth surface finish, low noise, and a soft and pliable feel. In some examples, an intermediate layer may be formed of predominately HPDE, MDPE or LDPE, or MDPE.

An intermediate layer formed of predominately MDPE may be particularly desired with one or more skin layers formed predominately of LLDPE because it imparts the intermediate layer with a good combination of relatively higher melt temperature, co-extrusion compatibility with the skin layer(s), pliability, toughness and tensile strength.

In alternative examples, an intermediate layer may be formed partially or predominately of a thermoplastic polymer other than polyethylene, such as any of the polymers identified above, or any polymers identified as suitable for intermediate layers in, for example, U.S. Pat. Nos. 9,169,366 and 5,261,899; and U.S. Pat. Apps. Pub. Nos. 2015/03433748; 2015/0104627; and 2012/0237746, including bio-polymers or polymers having bio-based content as described in the latter three publications, such as, but not limited to, polylactic acid and thermoplastic starch. Additionally, an intermediate layer may include recycled thermoplastic polymer of any of the above-described types.

For purposes of balancing economy of polymer usage and maximization of tensile strength of the film, it may be desired that the total caliper of the film fall within a range of from 40 µm to 100 µm, from 50 µm to 90 µm, or from 60 µm to 80 µm. For purposes of balancing economy of polymer usage, tensile strength and weldability, it may be desired that a three-layer film as described herein have a first and second skin layers each constituting from 15 percent to 35 percent of the weight of the film, and an intermediate layer constituting from 30 percent to 70 percent of the weight of the film.

Package Opening

Figure 6:
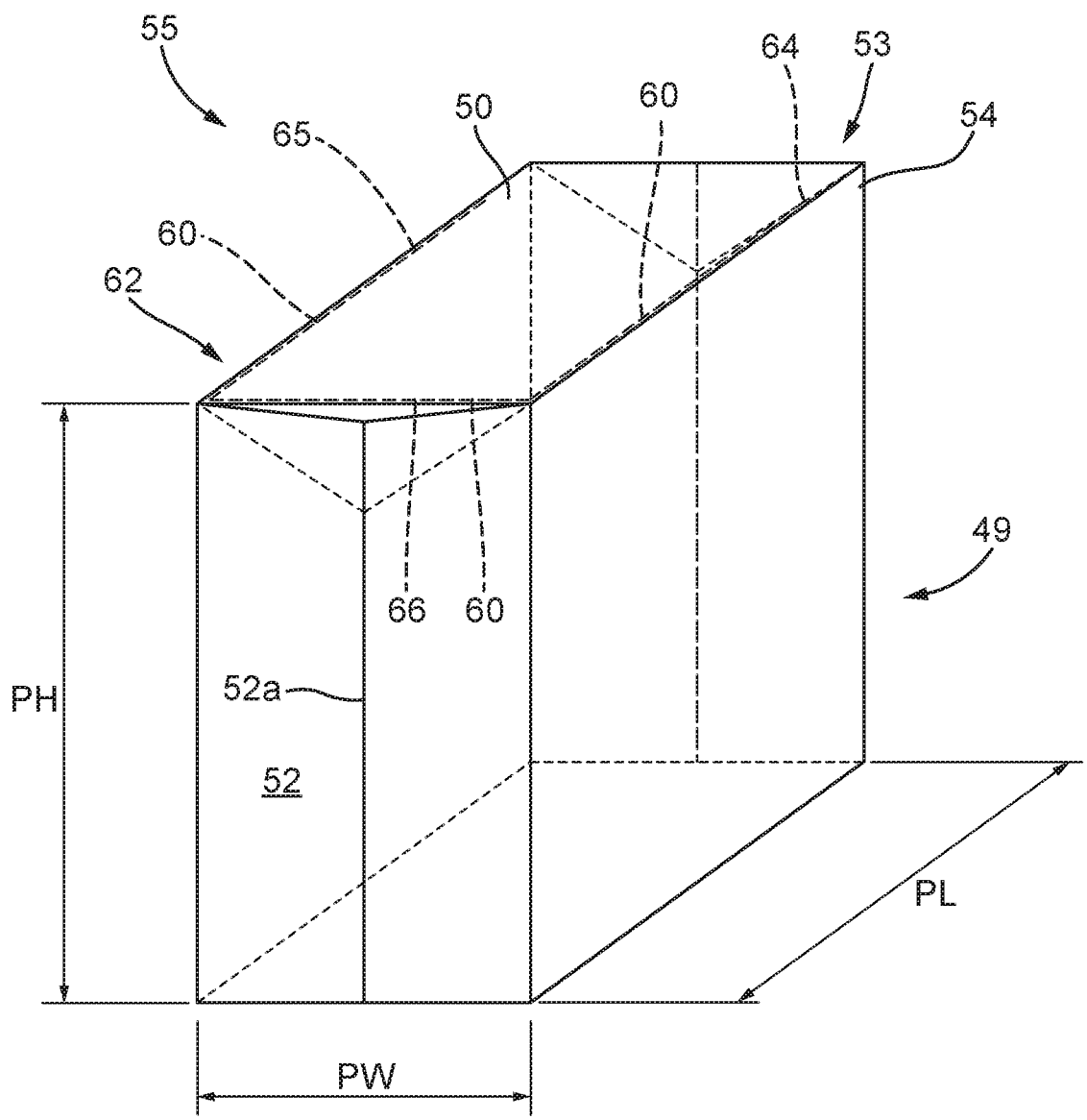
FIG. 6 is a perspective view of a film package that may be used to contain a stack of diapers such as the stack shown in FIG. 4, depicting a configuration of a path of perforations or scoring.

FIG. 6 shows a film package designed to contain a stack of disposable absorbent articles featuring perforations for easy opening of the pack. In the embodiment shown in FIG. 6, perforations 60 are provided along a periphery at a corner of the package intended to be opened by a user. As can be seen, in this embodiment, the perforations form an elongate "U" at the junction between the sides 54, 52, 55 of the pack and the top 50 of the pack and extending part way along the length of the front and back walls and across one of the side walls. It will be appreciated that there are many different variations of perforations or opening mechanisms that may be used.

The path 60 may be continuous. (For purposes herein, a "continuous" path of perforations or scoring is a singular path of individual, successive, mechanically-created partial or complete perforations, a singular path of individual, successive laser-scored partial or complete perforations, or a continuous, singular path of laser scoring, that is uninterrupted by an unperforated/unscored portion of the film of a length between successive perforations or scoring greater than 8 mm.) The opening perforations may be formed along the seam between the front, rear, side walls and upper surface. Alternatively, the opening perforations may be provided part way along the front, rear and side walls. Typically, the film package is designed to be opened in such a way that unused products may be retained within the package after initial opening and such that the package may be somehow closed to maintain the integrity of the products left therein.

Folding Tabs

FIGS. 7A to 7F show different variations of folding tabs as they may be applied to film packaging of the present invention. As previously described, there are multiple ways in which the folding tabs may be applied, some of which are described herein by way of example. In general, the folding tab(s) 100 have the following dimensions shown in FIG. 7A: Length (Tl), Height (Th), Thickness (or caliper) (Tc) and Distance from opening (To).

Figure 7A:
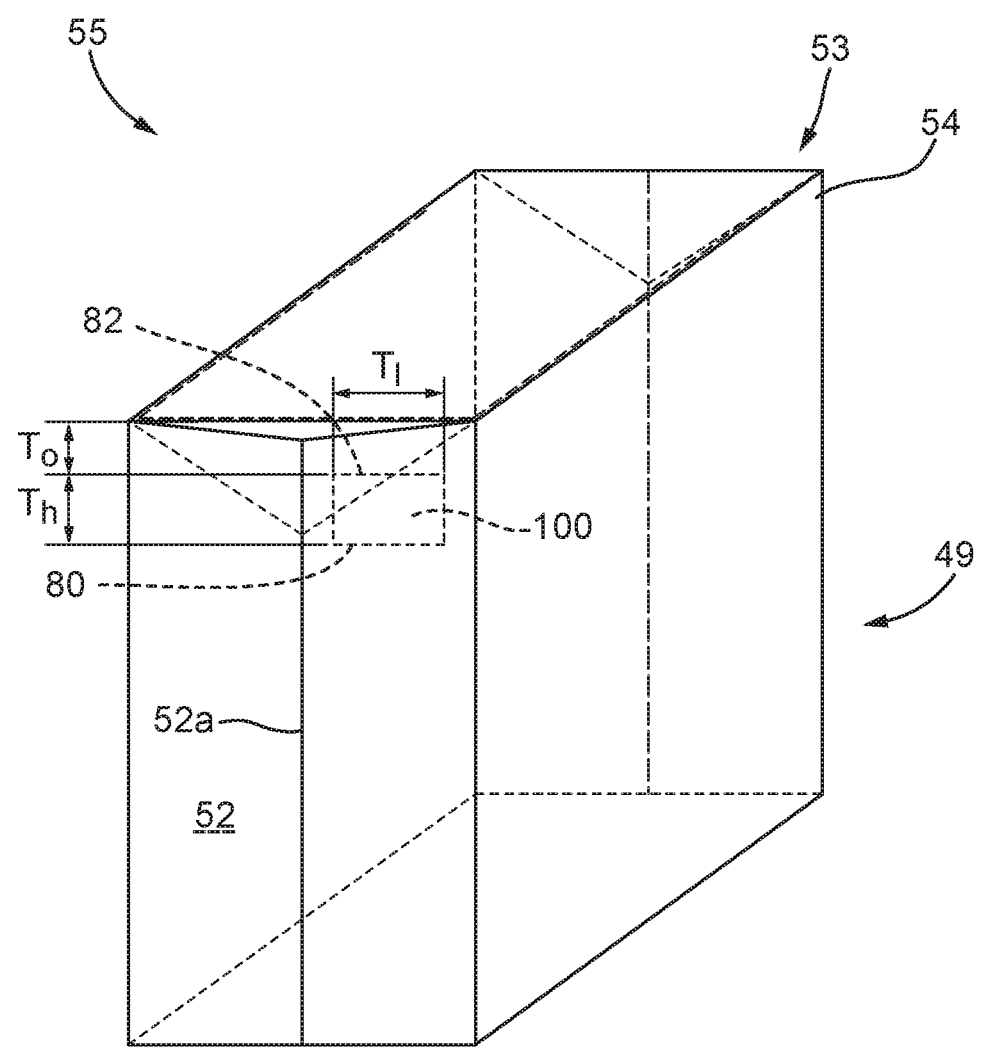
Figure 7C:
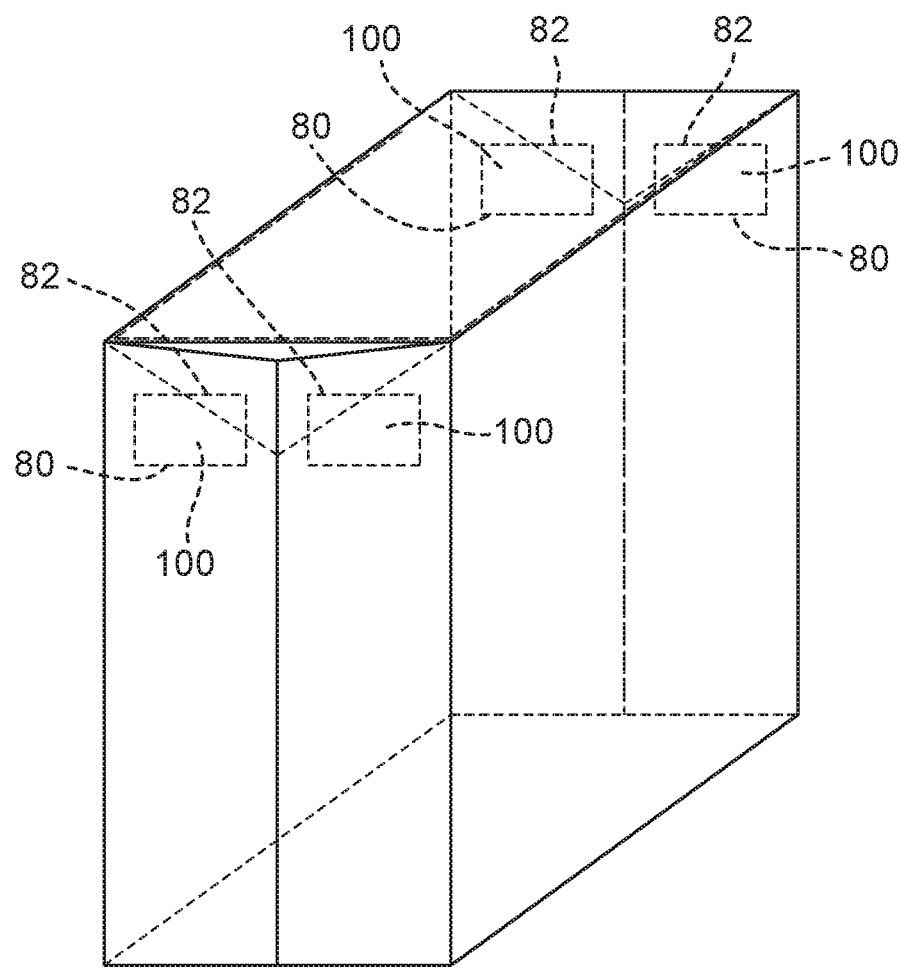

In FIG. 7A, the film package is provided with one folding tab 100 extending along a side wall 52 in a direction parallel to the opening of the package. The folding tab 100 in FIG. 7A extends between a seam 52A located midway along the side wall and the corner of the package between the side wall and the front or rear wall. FIG. 7B shows a variation having two folding tabs 100, one on each side wall between the seam and one of the front or rear walls. Although the folding tabs 100 are shown positioned diametrically opposite each other, it will be appreciated that they could likewise be positioned opposite each other (i.e., between the respective seams and just one of the front or rear wall). FIG. 7C shows an embodiment with four folding tabs 100, where each folding tab is positioned between a side wall seam and one of the front or rear wall (i.e. the corner where the front/rear wall meet one of the side walls). FIG. 7D shows an example with additional folding tabs 102 extending along the front and rear walls in a direction substantially parallel to the opening. By providing at least one folding tab on each of the side walls of the package, a user is easily able to push the front and rear walls together, either by folding the package in on itself about the seams (thereby creating a "w" of the side walls) or by pushing the package out at the seams (thereby elongating the front and rear panels). The user can then grip both folding tabs and fold the package over the tabs. The stiffness added to the flexible packaging by the one or more folding tabs provides rigidity about which the film package may be folded.

In the embodiments described above, the one or more folding tabs do not extend over either the seams 52 in the side walls or the corners where the side walls meet the front or rear walls of the package, i.e. they extend only over planar surfaces. In such embodiments, the length of the folding tab may be such that it extends the whole distance between adjacent bends in the package, whether the bend is caused by the fold in the side wall at a seam or at a corner of the package between side wall and front/rear wall. Alternatively, the folding tab(s) may extend just part way along any planar area.

Figure 8A:
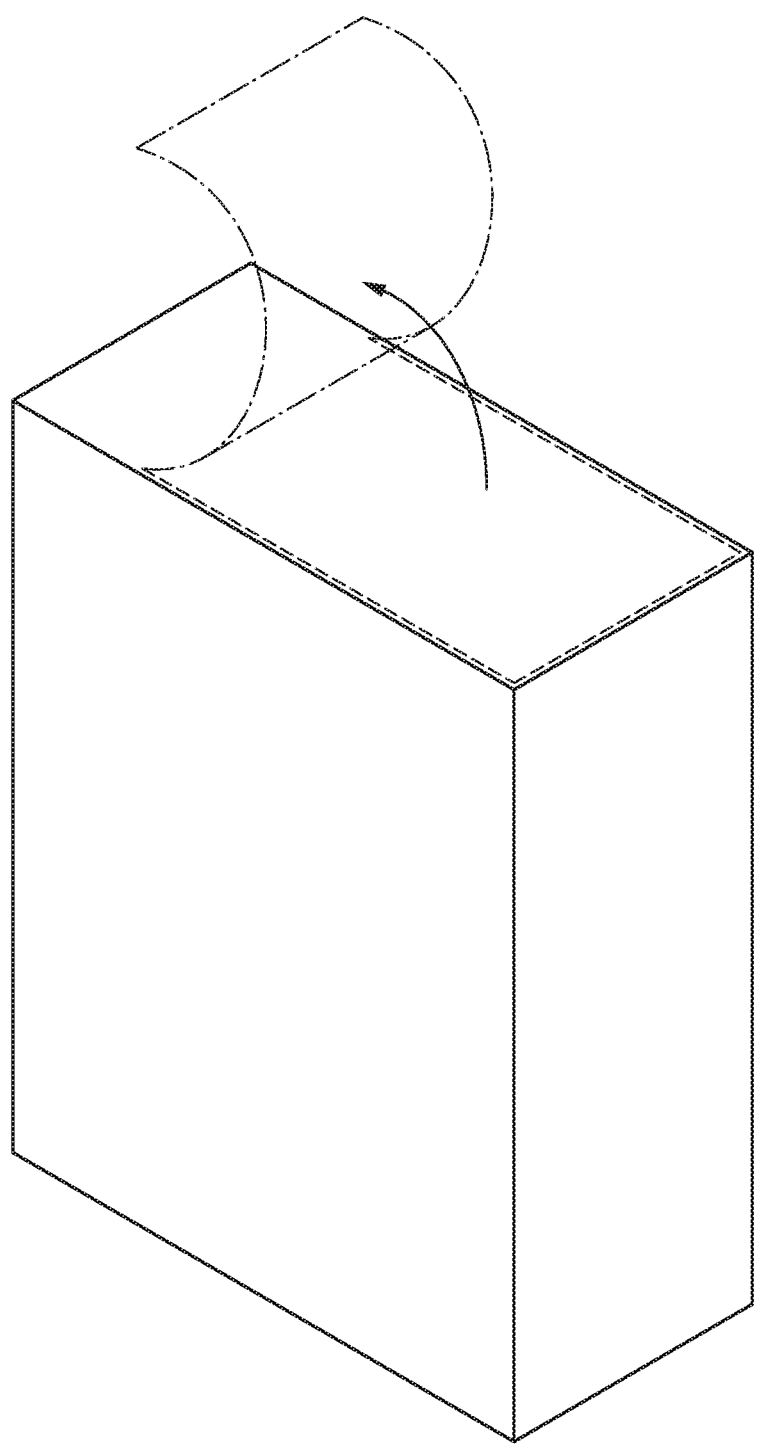
FIGS. 8A to 8E show schematically how the package may be folded over the folding tabs during use.
Figure 8B:
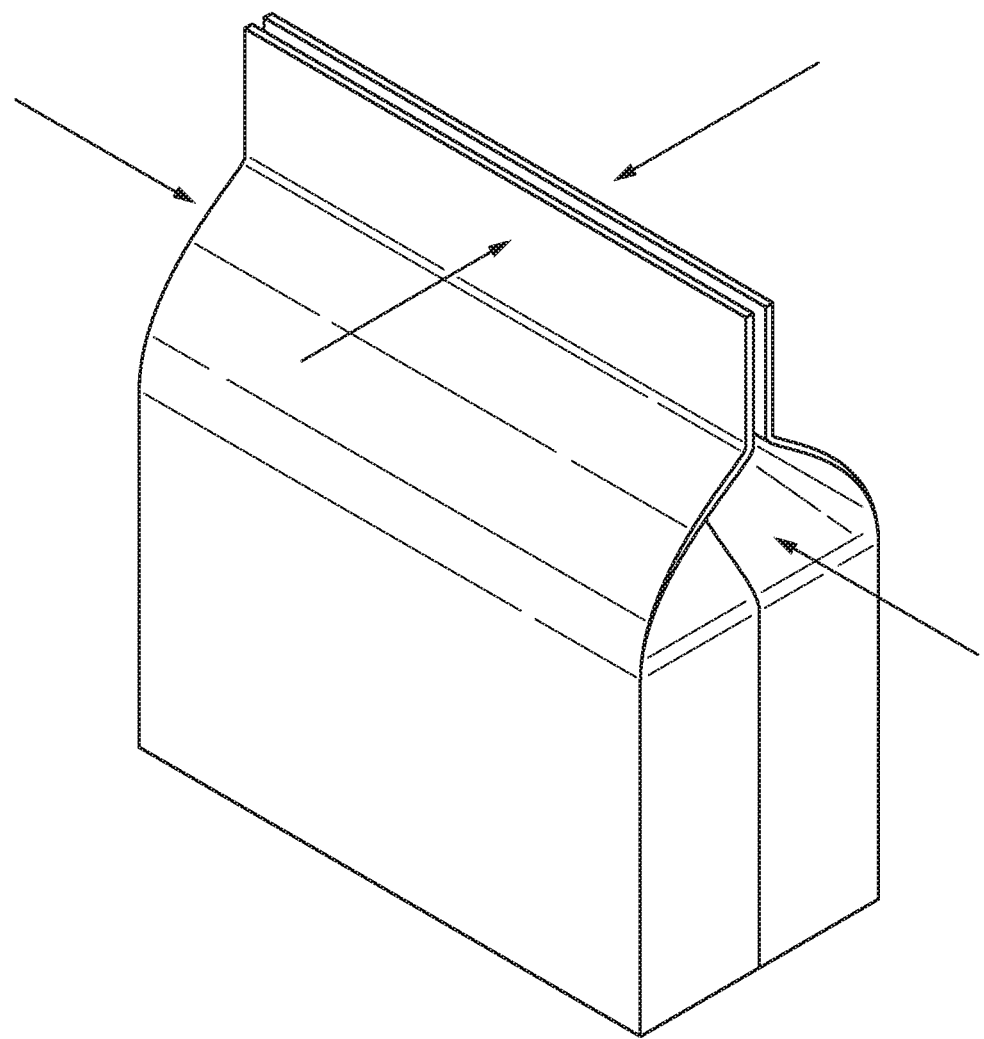
Figure 8C:
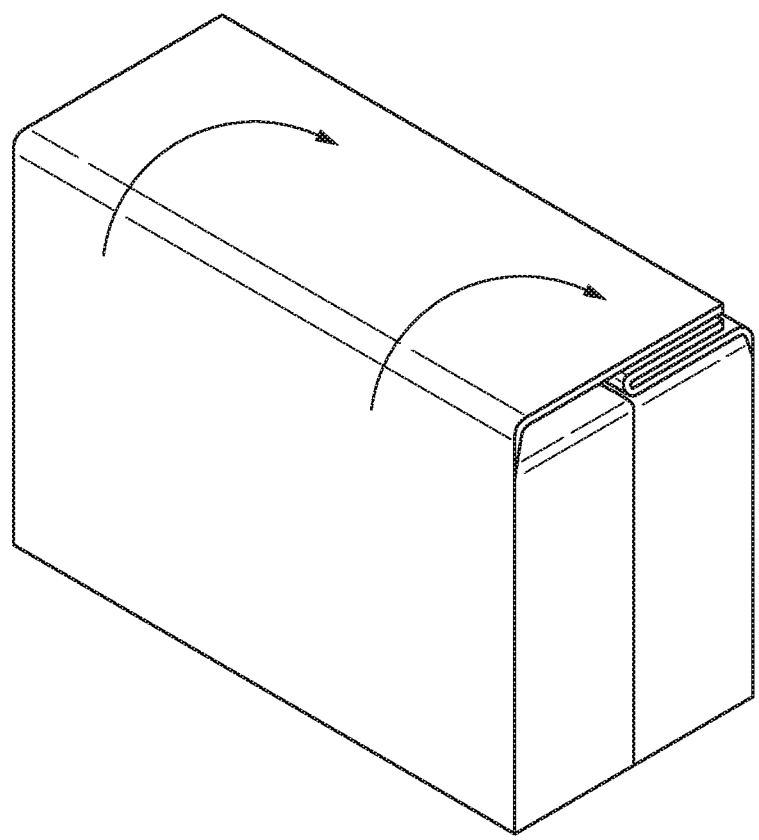
Figure 8D:
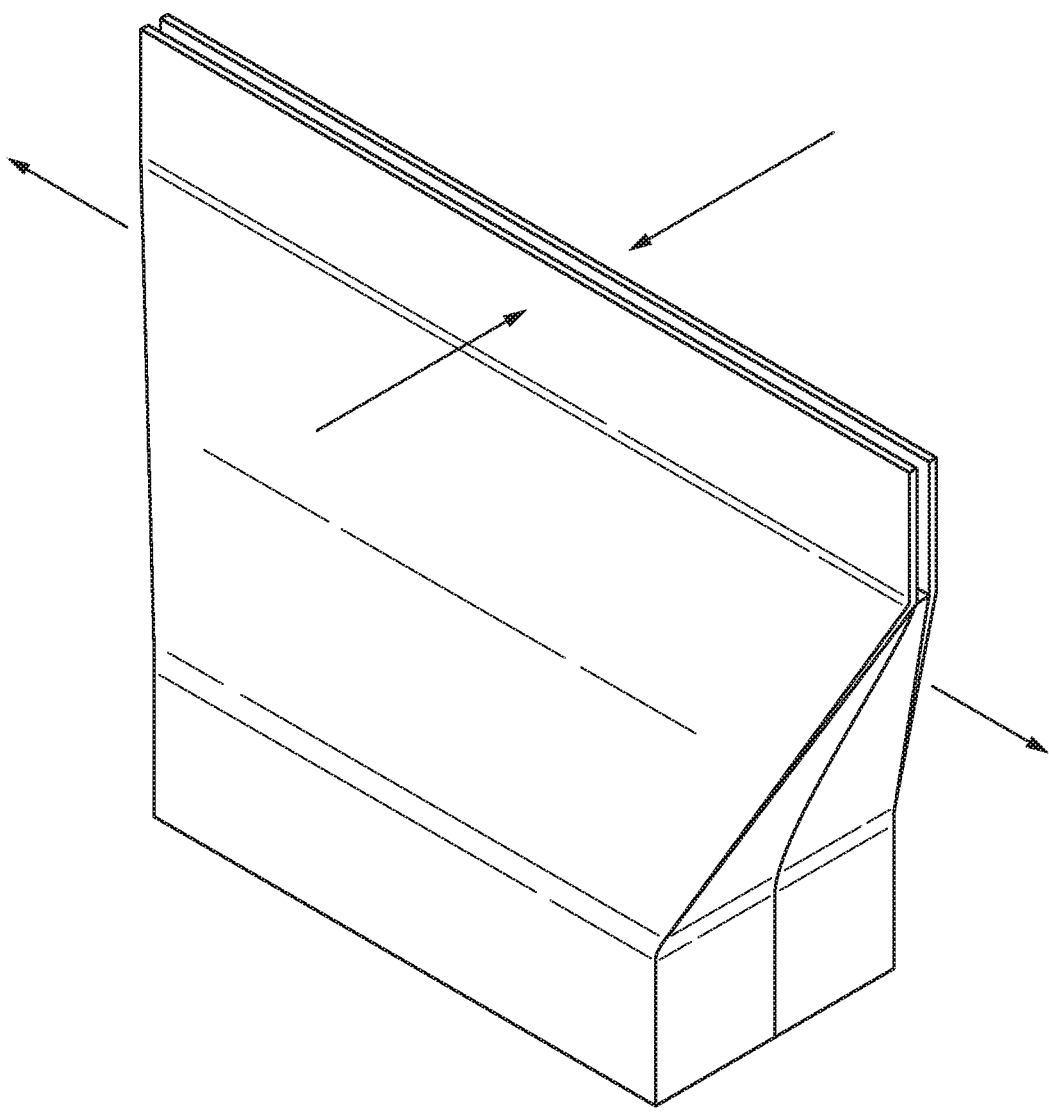
Figure 8E:
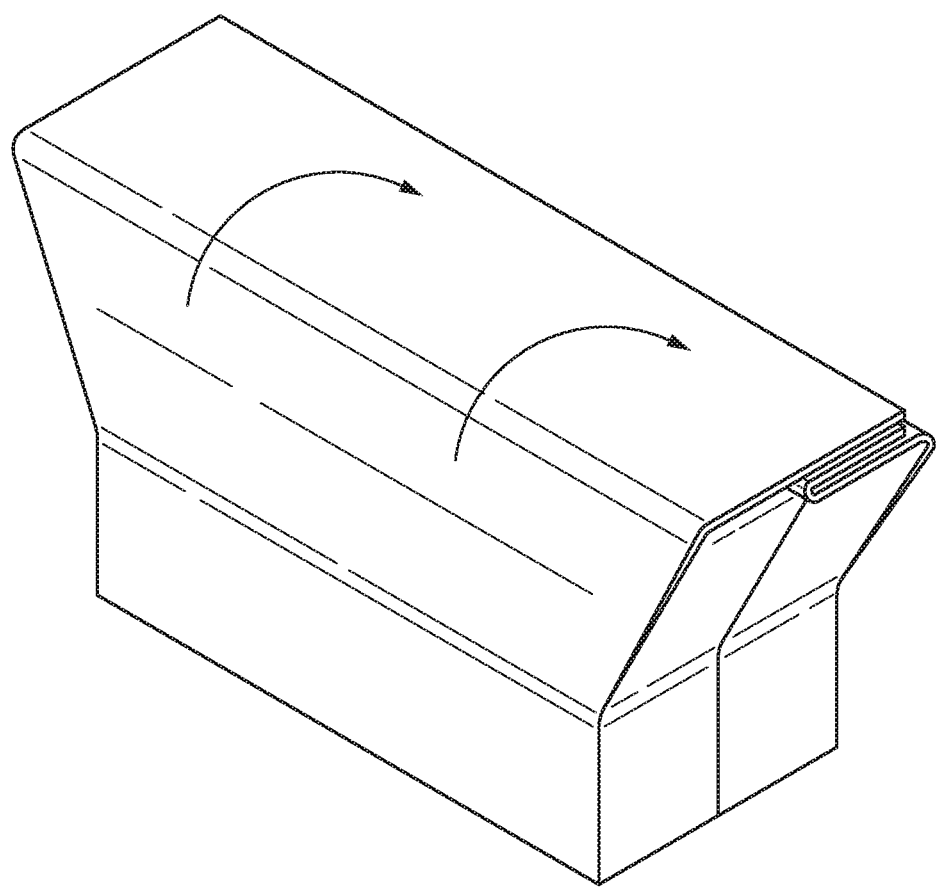

FIG. 7E shows a variation having elongate folding tabs 104 on each of the side walls, where the folding tabs extend over the seams or areas where the packaging is folded. Again, it will be appreciated that just one folding tab may be provided along one side wall. However, in some forms, one (or more) folding tab is provided along each side wall. The folding tabs of FIG. 7E are provided with weakened portions 106 at the point where the folding tab extends over the seam. The weakened portions allow some flexibility in movement of the folding tab(s) in places where it may need to be elongated or bent. For example, in the embodiment shown in FIG. 7E, the folding tabs retain a planar form while the package is in an open state, however, in a closed state, the folding tabs are bent (or folded) in on themselves. The same may be true for folding tabs that extend over any of the corners between the side walls and front/rear walls. For example, FIG. 7F shows an embodiment having two elongate tabs, both of which extend from one side wall to the other side wall. In such an embodiment, pre-defined weakened portions may not be required if, in a closed state, the side walls are pushed outwards to extend the front/rear walls (as shown in FIG. 8C), however, in the case where the side walls are to be pushed in to facilitate closing of the package (as shown in FIG. 8B), weakened portions may be provided to the folding tabs at the point(s) where they coincide with the corners between the side walls and front/rear walls.

Many mechanical treatments are known in the art for providing weakened portions, for example scoring, stretching, embossing, perforating etc. Such treatments may be applied to the folding tab prior to inclusion in the package. Alternatively, upon insertion of the folding tab, the folding tabs may be creased by pressing sides of the package together thereby forcing the folding tabs in on themselves and causing natural weakness about the folding points.

In each of the above described configurations, the front and rear walls of the film package will naturally incline towards each other as products are removed from the top of the package. As the front and rear walls move together (shown in FIG. 8A), the folding tabs provide a suitable structure about which the top of the package may be folded over on top of itself, as shown schematically in FIGS. 8A to 8D. Without being bound by theory, it is thought that the folding tab(s) provide some weight and rigidity to an upper part of the package that enables the front and rear walls to be brought together and folded over. Folding over the package once products have been removed from inside helps to retain hygiene of the products inside the package (e.g., by preventing dust from entering the package) and helps to reduce space occupied by the package.

In the accompanying drawings, the folding tabs are shown proximal the opening edge of the package. Space is created in the package as articles (e.g., diapers) are removed and the stack takes on more of a parallelogram shape vs a rectangular shape. It is possible to close the package by bringing together the front and rear walls and folding them over the one or more folding tabs once the top edge of the stack is beneath the lower edge of the folding tab(s). Thus, the folding tabs may be located immediately adjacent the opening and no more than 33% of the height of the package away from the opening and may be no more than 35%, 30%, 25%, 20% or 15% of the height of the package away from the opening. Where the folding tab(s) is located adjacent the opening, it provides additional reinforcement when a user tears the perforation by providing a stiffer area immediately below the perforation.

The folding tabs have a first edge 80 proximal to the top surface of the package and a second edge 82 distal to the top surface of the package and the height Th of the tab is the distance between the first edge and the second edge. The folding tabs may have a height of from 10 mm and 50 mm, 15 mm to 45 mm, 20 mm to 40 mm, 25 mm to 35 mm. In this respect and for ease of use, there is a balance between providing folding tabs that have sufficient height that provides a substantial tab about which to fold the package and not being able to close the package until the top edge of the stack is beneath the second edge of the folding tab(s). In an embodiment, the combined distance away from the opening and height of the folding tab(s) is less than 35%, 30%, 25% or 20% of the overall package height.

In the accompanying drawings, the folding tab is shown extending generally in parallel to the top edge of whichever wall it is positioned on. Although each of the folding tabs is shown as being uniform, it is appreciated that in alternative embodiments (not shown), the folding tab may not be rectangular, and instead may, for example, be shaped as a parallelogram or another shape consistent with the overall shape of the package.

The folding tab(s) is formed of material having different properties to that of the primary packaging material. Specifically, the folding tab(s) is formed of material that is stiffer than the packaging material, thus making it easier to fold the package material about the folding tab(s). In embodiments, the folding tab(s) have a thickness of less than 2.0 mm, 1.5 mm, 1.0 mm or 0.75 mm otherwise the folding tab(s) become too heavy and inconvenient to use. Furthermore, if the folding tab(s) are too thick, they may impede removal of diapers from the pack and result in additional waste material.

The folding tabs may be formed of a variety of materials, including one or more elastomeric bands or strands, a strip or layer of foam, a fibrous web (nonwoven or woven), a scrim, a polymeric film, a bead or line of cured polymer or hot-melt adhesive formulation (with or without a tackifier). Fibrous webs or scrims can comprise natural fibers (e.g., cotton or wood pulp), synthetic fibers, or a combination thereof. The fibrous web can be made through a wet laid process or a dry laid process. The folding tab(s) can be affixed to the package by any number of techniques, including, for example, through adhesive, ultrasonics, heat, pressure, and combinations thereof. In embodiments, the folding tab(s) are provided on the inside surface of the package, however, in alternative embodiments, the folding tab(s) may be provided on the outer surface of the package or on a combination of both.

Indicia on Packaging

It may be desired to provide one or more indicia on the package that visibly, tactilely and/or verbally identify the location of the path 60 of perforations or scoring. The one or more indicia may include, but are not limited to, an imprinted path marking or tracing path 60, of a color that visibly contrasts with surrounding package printing; tactilely perceivable indicia; verbal indicia; other graphic indicia or any combination thereof. In one example, the indicia may include embossing or other surface texturing of the film, configured to provide raised, tactilely perceivable features that suggest the presence of the path 60 of perforations or scoring for opening. In a particular example, embossing may be configured to suggest one or more ridges following lines or paths proximate and parallel to path 60. In another particular example, embossing may be configured to suggest one or more lines or paths of stitches following paths proximate and parallel to path 60. Additionally, the package may include verbal or graphic indicia that instruct or encourage the consumer to flip the package over, putting the perceived "top" side down and "bottom" side up, for opening and/or storage. Additionally, or alternatively, commercial artwork, graphics, and verbal information printed onto the film of the package may be configured in some examples to have an upright appearance regardless of which surface 50, 51 of the package is disposed at the top as the package is placed on a horizontal surface. In some examples, the printed material may be configured to suggest that either of surfaces 50, 51 can appropriately be deemed the "top" of the package.

The characteristic of the tactilely perceivable indicia and/or graphic indicia can vary significantly. The indicia can extend to a length that is less than, substantially the same as, or greater than a length of the path of perforations or scoring. In one example, a combination of tactilely perceivable indicia and graphic indicia are employed, wherein lengths of these two types of indicia are different. That is, graphic indicia may be included at a first length that does not disrupt the overall visual impression of the package artwork, and tactilely perceivable indicia is included at a second length that is greater than the first length. Alternative to or in addition to their respective extension lengths, positioning of the two types of indicia can vary on one or more of the package surfaces. For example, graphic indicia can primarily exists on a side surface (e.g., one of the third or fourth package surfaces) and optionally partially on an adjacent side surface (e.g., one of the fifth and sixth package surfaces and a package corner), while tactilely perceivable indicia primarily exists on a main package surface (e.g., one of the fifth and sixth package surfaces). In this scenario, a consumer's eyes are drawn to the graphic indicia to indicate where the path of perforations or scoring is located to help them to start the package opening process and then the consumer can utilize the tactilely perceivable indicia to guide their continued opening process to the fullest extent desired. By strategically locating the graphic indicia, artwork associated with a major package surface for marketing and educational purposes is not unduly disrupted by the graphic indicia. Thus, in one example, the package can comprise a first graphic comprising branding and marketing elements and a second graphic to highlight the path of perforations or scoring wherein the second graphic does not intersect the branding and marketing elements.

Other characteristics of the indicia can vary. For example, the graphic indicia can have varying color, hue, and/or dimensions. And the tactilely perceivable indicia can have varying dimensions (e.g., emboss depth), intensity, frequency or the like. Such characteristics can vary as step changes or gradually like in a gradient pattern.

While the disclosure thus far has focused on package forms comprising a path of perforations or scoring, alternative forms may employ mechanical fastening means to both open and reclose the package along a SLS, LSL, or combination SLS and LSL path. Examples of suitable mechanical fastening means includes zippers and tongue-and-groove type closures.

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package formed of a flexible polymeric film, the package comprising:
    a. a plurality of absorbent articles;
    b. the flexible polymeric film enclosing the plurality of absorbent articles to define a cuboid package having a top surface, a bottom surface, a front wall, a rear wall, a first side wall, and a second side wall;
    c. one or more folding tabs proximal to the top surface and extending along a portion of a width of one or both of the first and second side walls;
        wherein each folding tab has a height of between about 10 mm and about 50 mm in a direction perpendicular to a length of the folding tab, and wherein each folding tab has a higher bending stiffness than the flexible polymeric film; and
    d. a first seam and a second seam extending from a top surface to a bottom surface of the respective first and second side walls;
        wherein a single folding tab is provided extending along a portion of a width of three or more walls of the package, and wherein the single folding tab is provided with a weakened portion coincident with each junction between the first or second side walls and the front or rear walls and each seam over which the single folding tab extends.

2. The package of claim 1, wherein the one or more folding tabs are formed of a material selected from the group of: elastomeric bands, elastomeric strands, foam, nonwoven fibrous web, woven fibrous web, scrim, polymeric film, a bead of cured polymer, a line of cured polymer, and hot-melt adhesive formulation.

3. The package of claim 2, wherein the one or more folding tabs have a first edge proximal to the top surface of the package and a second edge distal to the top surface of the package, and wherein the distance between the first edge and the top surface is less than 33% of a total height of the package.

4. The package of claim 1, wherein the one of more folding tabs are adhered to an inside surface of the package.

5. The package of claim 1, wherein each of the one or more folding tabs extends along the portion of the width of at least one of the first and second side walls and one of the front and rear walls, and wherein each folding tab is provided with a weakened portion coincident with each junction between the first or second side wall and the front or rear walls and each seam.

6. The package of claim 1, wherein each folding tab provided on one of the first and second side walls extends between one of the first and second seams and the front wall or the rear wall.

7. The package of claim 6, wherein a first folding tab is provided on a first side surface, extending between the first seam and one of the front and rear walls and a second folding tab is provided on a second side wall, extending between the second seam and the other of the front and rear walls.

8. A package formed of a flexible polymeric film, the package comprising:
   a. a plurality of absorbent articles;
   b. the flexible polymeric film enclosing the plurality of absorbent articles to define a cuboid package having a top surface, a bottom surface, a front wall, a rear wall, a first side wall, and a second side wall;
   c. one or more folding tabs proximal to the top surface and extending along a portion of a width of one or both of the first and second side walls;
   wherein each folding tab has a height of between about 10 mm and about 50 mm in a direction perpendicular to a length of the folding tab, and wherein each folding tab has a higher bending stiffness than the flexible polymeric film;
   wherein the one of more folding tabs are adhered to an inside surface of the package; and
   d. a first seam and a second seam extending from a top surface to a bottom surface of the respective first and second side walls;
   wherein a single folding tab is provided extending along a portion of a width of three or more walls of the package, and wherein the single folding tab is provided with a weakened portion coincident with each junction between the first or second side walls and the front or rear walls and each seam over which the single folding tab extends.

9. The package of claim 8, wherein the one or more folding tabs are formed of a material selected from the group of: elastomeric bands, elastomeric strands, foam, nonwoven fibrous web, woven fibrous web, scrim, polymeric film, a bead of cured polymer, a line of cured polymer, and hot-melt adhesive formulation.

10. The package of claim 9, wherein the one or more folding tabs have a first edge proximal to the top surface of the package and a second edge distal to the top surface of the package, and wherein the distance between the first edge and the top surface is less than 33% of a total height of the package.

11. The package of claim 8, wherein each folding tab provided on one of the first and second side walls extends between one of the first and second seams and the front wall or the rear wall.

12. The package of claim 11, wherein a first folding tab is provided on a first side surface, extending between the first seam and one of the front and rear walls and a second folding tab is provided on a second side wall, extending between the second seam and the other of the front and rear walls.

13. A package formed of a flexible polymeric film, the package comprising:
   a. a plurality of absorbent articles;
   b. the flexible polymeric film enclosing the plurality of absorbent articles to define a cuboid package having a top surface, a bottom surface, a front wall, a rear wall, a first side wall, and a second side wall;
   c. one or more folding tabs proximal to the top surface and extending along a portion of a width of one or both of the first and second side walls;
   wherein each folding tab has a height of between about 10 mm and about 50 mm in a direction perpendicular to a length of the folding tab, and wherein each folding tab has a higher bending stiffness than the flexible polymeric film; and
   d. a first seam and a second seam extending from a top surface to a bottom surface of the respective first and second side walls;
   wherein each of the one or more folding tabs extends along a portion of a width of at least one of the first and second side walls and one of the front and rear walls, and wherein each folding tab is provided with a weakened portion coincident with each junction between the first or second side wall and the front or rear walls and each seam.

14. The package of claim 13, wherein the one or more folding tabs are formed of a material selected from the group of: elastomeric bands, elastomeric strands, foam, nonwoven fibrous web, woven fibrous web, scrim, polymeric film, a bead of cured polymer, a line of cured polymer, and hot-melt adhesive formulation.

15. The package of claim 14, wherein the one or more folding tabs have a first edge proximal to the top surface of the package and a second edge distal to the top surface of the package, and wherein the distance between the first edge and the top surface is less than 33% of a total height of the package.

16. The package of claim 13, wherein each folding tab provided on one of the first and second side walls extends between one of the first and second seams and the front wall or the rear wall.

17. The package of claim 16, wherein a first folding tab is provided on a first side surface, extending between the first seam and one of the front and rear walls and a second folding tab is provided on a second side wall, extending between the second seam and the other of the front and rear walls.

\* \* \* \* \*